United States Patent
Axon

(10) Patent No.: US 11,399,712 B2
(45) Date of Patent: Aug. 2, 2022

(54) MEDICAL SCOPE ACCESSORY, MEDICAL SCOPES COMPRISING THE ACCESSORY, AND USE THEREOF

(71) Applicant: ARC MEDICAL DESIGN LIMITED, Leeds (GB)

(72) Inventor: Patrick Axon, Leeds (GB)

(73) Assignee: ARC MEDICAL DESIGN LIMITED, Leeds (GB)

(*) Notice: Subject to any disclaimer, the term of this patent is extended or adjusted under 35 U.S.C. 154(b) by 933 days.

(21) Appl. No.: 16/099,695

(22) PCT Filed: May 12, 2017

(86) PCT No.: PCT/GB2017/051341
§ 371 (c)(1),
(2) Date: Nov. 8, 2018

(87) PCT Pub. No.: WO2017/194970
PCT Pub. Date: Nov. 16, 2017

(65) Prior Publication Data
US 2019/0183328 A1 Jun. 20, 2019

(30) Foreign Application Priority Data
May 12, 2016 (GB) .................................... 1608380

(51) Int. Cl.
*A61B 1/32* (2006.01)
*A61B 1/00* (2006.01)
(Continued)

(52) U.S. Cl.
CPC .............. *A61B 1/32* (2013.01); *A61B 1/0014* (2013.01); *A61B 1/00087* (2013.01);
(Continued)

(58) Field of Classification Search
CPC ............ A61B 1/00087; A61B 1/00089; A61B 1/00101; A61B 1/31
See application file for complete search history.

(56) References Cited

U.S. PATENT DOCUMENTS

2011/0004058 A1 1/2011 Oneda et al.
2011/0009696 A1 1/2011 Miyoshi
(Continued)

FOREIGN PATENT DOCUMENTS

AU 2015203443 A1 7/2015
GB 2497544 A 6/2013
(Continued)

OTHER PUBLICATIONS

Office Action issued in corresponding Japanese Patent Application No. JP2019-511818 dated Apr. 20, 2021 (with English translation)(7 pages).
(Continued)

*Primary Examiner* — Matthew J Kasztejna
(74) *Attorney, Agent, or Firm* — Kilyk & Bowersox, P.L.L.C.

(57) ABSTRACT

A cover (1) for a shaft of a medical scoping device comprises tubular member (2) arranged for application on the distal tip of the medical scoping device. The cover (1) comprises a plurality of projecting elements (3) spaced apart circumferentially around the tubular member (2), each projecting element having a base portion (13) and an arm portion (14). The projecting elements are pivotably mounted on the tubular member about a pivot axis. The base portion (13) comprises a detent (20), and the tubular member comprises a contact region, for example a protuberance (23), said contact region being located such that pivoting move-
(Continued)

ment of the projecting element for moving the arm portion in a distal direction can effect impacting of the detent (20) on the contact region (23).

26 Claims, 12 Drawing Sheets

(51) Int. Cl.
*A61B 1/31* (2006.01)
*A61B 17/00* (2006.01)
*A61B 90/00* (2016.01)

(52) U.S. Cl.
CPC ...... *A61B 1/00089* (2013.01); *A61B 1/00101* (2013.01); *A61B 1/31* (2013.01); *A61B 2017/00296* (2013.01); *A61B 2090/3966* (2016.02)

(56) References Cited

U.S. PATENT DOCUMENTS

| | | |
|---|---|---|
| 2012/0197083 A1 | 8/2012 | Spenser |
| 2014/0046139 A1 | 2/2014 | Cole et al. |
| 2014/0187939 A1 | 7/2014 | Ogawa |
| 2015/0148606 A1 | 5/2015 | Rottenberg et al. |
| 2017/0112365 A1* | 4/2017 | Ostrovsky ............... A61B 1/32 |
| 2018/0008128 A1* | 1/2018 | Axon ...................... A61B 1/31 |
| 2018/0078120 A1* | 3/2018 | Poll ................... A61B 1/00105 |

FOREIGN PATENT DOCUMENTS

| | | |
|---|---|---|
| JP | 2003033319 A | 2/2003 |
| JP | 2003180611 A | 7/2003 |
| JP | 2003339631 A | 12/2003 |
| JP | 2009018068 A | 1/2009 |
| WO | 2011148172 A2 | 12/2011 |
| WO | 2013190543 A1 | 12/2013 |
| WO | 2014123563 A1 | 8/2014 |
| WO | 2015160970 A1 | 10/2015 |

OTHER PUBLICATIONS

International Search Report and Written Opinion issued in corresponding International Patent Application No. PCT/GB2017/051341 dated Jul. 31, 2017 (14 pages).
Innomedicus Nata: "innoMedicus—Endocuff Animation V131210," youtube, 2013, XP054977549, Retrieved from the Internet: URL:https://www.youtube.com/watch?v=Nx1Sp4Qjlms.
Search Report issued in corresponding United Kingdom Patent Application No. GB 1608380.0 dated Nov. 7, 2016 (5 pages).
Search Report issued in corresponding United Kingdom Patent Application No. GB 1707697.7 dated Oct. 27, 2017 (5 pages).
"Endocuff," ARC Medical Design Ltd., 2017, Retrieved from the Internet: URL:https://www.endocuff.com/products/endocuff/2, 'Endocuff' product webpage located at: www.endocuff.com/products/endocuff2 archived by Archive.org on Mar. 10, 2016, available at: http://web.archive.org/web/20160310011241/http://www.endocuff.com/products/endocuff/2 [Accessed on Nov. 2, 2016].
"Endocuff," ARC Medical Design Ltd., 2017, Retrieved from the Internet: URL:https://www.vimeo.com/142274388.

* cited by examiner

Section V-V

Section VII-VII

Section A-A

MEDICAL SCOPE ACCESSORY, MEDICAL SCOPES COMPRISING THE ACCESSORY, AND USE THEREOF

This application is a National Stage Application of PCT/GB2017/051341, filed May 12, 2017, which claims priority to United Kingdom Patent Application No. 1608380.0, filed May 12, 2016.

FIELD OF THE INVENTION

The present invention relates to a device for use with a medical scoping device shaft and to a medical scoping device including a said device.

BACKGROUND OF THE INVENTION

In endoscopic examinations/procedures, flexible instruments designed to view the gastrointestinal tract are inserted along a body cavity to an internal part such as the stomach, duodenum, small intestine or large intestine. The instruments are provided with imaging devices, for example fibre-optic or charge-couple device (CCD) cameras, which enable images to be transmitted around bends and images to be produced to a display screen. Accordingly, it is possible to view the inside surfaces of the oesophagus, stomach and duodenum using a gastroscope, the small intestine with an enteroscope, part of the colon using a flexible sigmoidoscope and the whole of the large intestine (the bowel) with a colonoscope.

Enteroscopy is the endoscopic examination of the small intestine whereas colonoscopy is the endoscopic examination of the colon and the distal part of the small bowel and flexible sigmoidoscopy is the examination of the rectum and lower part of the bowel. Each scoping procedure may provide a visual diagnosis (e.g. ulceration, polyps) and grants the opportunity for biopsy or removal of suspected lesions. Whilst colonoscopic and enteroscopic examinations are the most effective techniques to assess the state of health of the bowel, they are inconvenient, uncomfortable, expensive procedures that are associated with significant risks of potentially serious complications. The most common complications are: failure to achieve a complete examination (5-10%); failure to detect a polyp (up to 20%); reaction to intravenous drugs; over-sedation leading to hypoxia and cardio-vascular collapse; splenic injury (rare); bowel perforation, (1 in 500-1500); full thickness burn (uncommon) and; bleeding following polypectomy.

The anatomy of the intestine is such that the lining is formed into folds. In the small intestine the folds are essentially permanent and are not smoothed out when the intestine is extended. In contrast, extending of the colon results in the colonic folds collapsing. In all endoscopic examinations, folds present may hamper the endoscopist's ability to visualise the entire surface of the mucosa and in particular, detect pre-malignant and malignant lesions tucked away on the proximal face of these folds during extubation.

WO2011/148172 discloses a covering for a shaft of a medical scoping device in the form of a cuff which is mountable near the tip of the shaft and which comprises a multiplicity of projecting elements positioned in one or more circumferentially extending rings around the cover. The projecting elements are movable from a rest position to a position in which they point towards the proximal end of the shaft and a position in which they extend distally. The projecting elements, in use, become fanned out to provide support for and dilate a lumen wall of a body passage into which the scoping device has been inserted. As the tip of the endoscope passes along the lumen during withdrawal, the folds may be flattened further enhancing visualisation.

The device of WO2011/148172 has been found to have considerable advantages in terms of facilitating entry and exit of the medical scoping device shaft to which it is attached, and improving visualisation. Nonetheless, further improvement in visualisation would be advantageous. In addition, or instead, in some circumstances, a different range of movement of the projecting elements could offer advantages.

WO2014/123563 discloses an endoscopic sleeve having projections in the form of full rings or partial rings about a central sleeve, the rings being flexible. The rings or partial rings may be connected to the sleeve through a root portion which facilitates bending. However, in practice, the rings or partial rings can collapse only to a relatively limited extent. The remaining relatively large overall diameter of the sleeve including the collapsed rings is undesirable. A smaller diameter is desirable in order to minimise patient discomfort when the scope and mounted device pass through constricted areas such as the sphincter or sharp bends within the cavity to be examined.

SUMMARY OF THE INVENTION

The invention provides a cover for a shaft of a medical scoping device, the cover comprising a tubular member arranged for application over a distal tip of the medical scoping device shaft with the tubular member, in use, extending along a portion of the length of the distal end of the shaft, the tubular member comprising a proximal circumferential edge, a distal circumferential edge, an inner surface at least a part of which grips the shaft, and an outer surface, the cover comprising a plurality of projecting elements spaced apart circumferentially around the tubular member, each projecting element having a base portion and an arm portion, the base portion comprising first and second mountings by which the projecting element is pivotably mounted on the tubular member about a pivot axis, wherein the base portion comprises a detent, and wherein the tubular member comprises a contact region, said contact region being so located that pivoting movement of the projecting element for moving the arm portion in a distal direction can effect impacting of said detent on said contact region.

In use of the cover of the invention the locus of movement of each of the projecting elements is limited by the interaction of the detent with the contact region on the tubular member. On pivoting movement of a projecting element towards the distal direction, the detent will impact on the contact region, thereby hindering further pivoting movement of the base of the projecting element. Movement of the rest of the projecting element may, however, be unaffected by the detent. Thus, for example, in the preferred arrangement in which the projecting elements are flexible, the projecting elements may still be capable of being everted such that their distal tips are directed distally with regard to the scope shaft. Accordingly, the base portion of the projecting element can be movable through an angular range having a first, proximal range in which the base portion is relatively freely pivotable and a second, distal range in which, following initial impact of the detent on the contact region, the continued distal movement of the base portion by pivoting is resisted or even stopped. The greater resistance to movement towards the distal direction may be advantageous in terms of controlling the position and movement of the projecting elements in use, for example enabling increased opening force to be applied to folds of the cavity wall for opening folds and/or giving increased resistance to withdrawal of the scope which can enable more effective examination. In the second, distal angular range, even if further pivoting at the mountings is reduced or prevented, in the case of flexible projecting elements, further distal bending of the remainder of the projecting element may still be achievable through bending of the projecting element at an intermediate position displaced from the base, rather than primarily by bending at the base of the projecting element. That can advantageously reduce any tendency of the projecting elements, during retraction of the scope, to come into contact with the distal edge of the cover. It may also reduce the tendency for the projecting elements to contact, or to bend across immediately in front of, the distal surface. The positioning of the projecting elements is thus better controllable to obtain a desired interaction with the surrounding cavity wall and/or to achieve visualisation of the distal ends of the projecting elements within a desired range of positions relative to the tip of the scope. The present invention thus offers the possibility of improved visualisation by the clinician.

The invention further includes a method of examination of a cavity, for example a body cavity of a human or a non-human animal, which method comprises insertion of an endoscopy device comprising a cover according to the invention into said cavity, and causing everting of the projecting elements of said cover, wherein the angle of inclination of the base portions of the projecting elements when everted is limited to not more than 140°.

DETAILED DESCRIPTION

In this specification the words "distal" and "proximal" are defined with reference to a clinician who, in use, is operating the scoping device. The term "proximal" refers to a position or element that is closer to the operating clinician, and the term "distal" refers to a position or element that is further away from the operating clinician.

The expression "pivot axis" is used herein as referring to an axis about which turning may occur, and is not to be understood as requiring relative movement of separate parts. Indeed, in general pivot axes referred to herein are axes which are nominal axes about which turning can take place within a monolithically formed article. The terms "pivotable", "pivotably", "pivoting", and "pivot" are to be correspondingly understood.

The cover of the invention preferably has a multiplicity of projecting elements arranged in a ring around the cover. In practice, the cover will usually comprise from three to ten, preferably at least four, more preferably at least six projecting elements. It is preferred that each of the projecting elements is identical, although the invention is not limited to covers in which all the projecting elements are identical. The description of a projecting element and its mounting below is to be understood as preferably being applicable to all projecting elements of the cover, but for the avoidance of doubt, covers in which one or more projecting elements that are present are differently constructed are not excluded.

The projecting elements are mounted by means of first and second mountings to permit pivoting movement of the projecting element about a pivot axis.

Advantageously the first and second mountings are positioned on opposed surfaces of the base portion, the pivot axis being defined between the mountings and extending through the intervening base portion. Advantageously, the detent is located on an opposite side of the pivot axis from said arm portion. In consequence, pivoting movement of the projecting element forward towards the distal direction will generally result in pivoting of the detent in a different direction.

Advantageously, at least one of said detent and said contact region is resiliently deformable. Preferably both are resiliently deformable, at least in the region of contact.

Advantageously, said contact region comprises a protuberance. The protuberance provides a region that is elevated relative to at least a part of the surrounding surface to provide a clearly defined contact region. Advantageously, the protuberance comprises a portion that extends distally beyond the base portion of the projecting element. Preferably the contact region is integrally formed with the tubular member. More especially, the contact region, the protuberance if present, and the projecting elements are preferably integrally formed with the tubular member.

Advantageously, a respective contact region is so located relative to the respective projecting element that it delimits the locus of movement of at least the base portion of the said projecting element.

The projecting elements are spaced circumferentially about the tubular member. In one embodiment, the projecting elements are spaced apart in a ring around the tubular member. For example, in an illustrative arrangement in which there are eight projecting elements, the central axes of each adjacent pair of projecting elements subtend an angle of 45° at the centre of the tubular member. In other embodiments, the projecting elements may be circumferentially spaced about the tubular member in a pattern that includes one or more projecting elements that is/are spaced from the distal edge by a greater distance than one or more other projecting elements. For example, the projecting elements may be spaced from one another in a helical arrangement. Advantageously, the said ring or at least some of the said helically arranged projecting elements are spaced from the distal edge of the tubular member by a distance that is less than the length of the projecting elements. It is desirable for the cover to be positioned close to the tip of the scope on which it is mounted. That may serve to reduce the discomfort of insertion of the tip of the scope through the musculature on entry to the gastrointestinal tract. The tip is typically provided with a front surface through which imaging can be achieved, for example a lens through which visualisation can take place. Positioning of the projecting elements relatively close to the scope tip enables optimal benefit to be obtained from the action of the projecting elements in the opening up of tissue structures to improve visualisation and/or the maintenance of the desired position of the scope tip within the cavity being examined. Preferably, the projecting elements of a said ring or of a said helical arrangement are located no more than 10 mm from the distal edge of the tubular member.

In practice, the cover will typically extend along a relatively short portion (for example up to 2 or up to 3 cm in length) of the distal tip of the scope shaft on which it is mounted, for example a short length of the shaft immediately behind the distal tip of the shaft. Whilst it is preferable to apply the cover at a position on the scope that is close to the distal tip of the scoping device, it will be appreciated that the cover of the device may if desired be positioned differently on the scope. For example the cover may be so positioned on the scope that the distal edge of the tubular member is set back from the distal tip of the scope. The distal edge may, for example, be set back from the tip at least so as to ensure that the distal edge of the cover does not cover or interfere with visualisation at the front surface. In some circumstances the cover may even be set back from the distal end of the scope by a greater distance, for example 10 mm or more. In certain advantageous embodiments the distal edge is bevelled. That further reduces the tendency for undesirable interaction between the projecting elements and the distal edge when the projecting elements are deflected into a distal position or into the field of view.

Advantageously, the cover comprises on its outer surface a multiplicity of channels extending axially relative to the tubular member, each channel being defined between a pair of axially extending channel walls, and each projecting element being mounted in a said channel. Advantageously, each projecting element is mounted between a said pair of channel walls by means of said first and second mountings. The first and second mountings may, for example, comprise opposed connector portions on the base portion that extend between the base portion and the channel walls. Where present, the connector portions are advantageously formed integrally with the rest of the device and are resiliently deformable by twisting so as to permit pivoting of the projecting element about a pivot axis extending through the base portion, between the opposed connector portions.

The cover preferably comprises a multiplicity of spaced longitudinally extending ridges, the said channel walls each being formed by lateral surfaces of a respective said longitudinally extending ridge. Advantageously, each contact region is provided in a respective channel.

Advantageously, the or each projecting element comprises a tip portion and an intermediate portion between said base portion and said tip portion, the base portion, intermediate portion and tip portion being resiliently deformable. In practice, the tip portion will include a free end of the projecting element. The degree of freedom of movement of the projecting element in practice will be greater in the intermediate and tip portions as a result of the impeding of the movement of the base portion consequential to the impacting of the detent on the contact region of the cover. The projecting elements are preferably elongate in configuration. For example, they may advantageously have an aspect ratio (ratio of length to maximum width) of no less than three, preferably no less than four.

Advantageously, each projecting element is movable from a resting position to a proximal position in which its tip portion is directed in a proximal direction towards a proximal end of the scoping device shaft and is movable in a distal direction to a forward position in which the detent of the base portion of the respective projecting element abuts the corresponding contact region. Advantageously, on movement of the projecting element to said forward position, the detent impacts on the corresponding contact region when the projecting element, or at least the base portion thereof, is at an angle of from 80° to 140° relative to the proximal direction, whereby the contact region impedes further forward movement of the base portion beyond said angle. In an advantageous embodiment, the detent is so arranged and so movable relative to the contact region that on moving towards the forward position the detent first impacts on the contact region when the base portion of the projecting element is at an angle of from 90° to 160°, for example up to 150° or up to 140°, relative to the proximal direction. In certain advantageous embodiments the detent and/or contact region are resiliently deformable. For example, one or both of the detent and/or contact region may be resiliently deformable so as to permit further forward movement of said base portion through an angle of at least 10°, for example at least 20°, at least 30° or at least 40°. In certain embodiments, the detent of the projecting element may, on the projecting element being moved distally, first impact on the corresponding contact region when the projecting element, or at least the base portion thereof, is at an angle of from 80° to 120°, for example 90° to 110° relative to the proximal direction. In an illustrative embodiment the detent may impact on the contact region when the base portion is at an angle in the range of 90° to 120° to the proximal direction, and further pivoting towards the distal direction is permitted, for example, by resilient deformation of the detent or contact region, to a position in which the base portion is at an angle in the range of about 140° with reference to the proximal direction. Advantageously, the detent and contact region are so arranged that distal movement of said base portion beyond about 160° is prevented. That reduces any tendency of the projecting elements, during retraction of the scope, to come into contact with the distal edge of the cover. It also reduces any tendency for the projecting elements to fold over the tip and across the tip surface itself since the restriction on the mobility of the base portion limits the locus of movement of the intermediate and tip portions of the projecting elements which, when they are in view through the tip, will consequently tend to be spaced from the tip surface. That facilitates operations that involve a need to visualise the tip of the projecting element, for example manipulation of the scope tip to open colonic folds to view a hidden polyp, or use of a projecting element with a measuring scale to measure polyp size as described further below.

On insertion through the anus of a scoping device carrying a cover of the invention, the projecting elements are easily deflected towards the proximal direction without any obstruction by a combination of pivoting at the mountings and deformation or bending of the projecting elements themselves. On withdrawal of the scoping device and cover, the projecting elements are initially deflected towards the distal direction as a result of frictional force between the projecting element and the cavity wall through a combination of pivoting at the mountings and deformation or bending of the projecting elements. However, as a result of impacting of the detent on the corresponding contact region, pivoting is, after the point of impact, initially limited to that permitted by the detent and contact region, as for example by resilient deformation of one or both of the detent and contact region, with pivoting beyond a certain point being prevented; after the point of impact, further deflection of the elements typically requires deformation or bending of the projecting elements themselves and the force required to do that may be greater than the force required for pivoting. In this way, the device has a substantially greater resistance to deflection of the projecting elements in the distal direction than in the proximal direction.

The dimensions of the cover may to some extent depend on the type of scope with which it is to be used. The cover may, by way of example, have a total axial length of at least 10 mm, for example, in the range of from 10 to 20 mm. The internal diameter should advantageously be such that, when in position on the scope to be used, the cover is slightly elastically radially expanded, as that provides a close fit on the scope and more reliable and reproducible movement of the projecting elements. Whilst the internal diameter will be selected according to the scoping device with which the cover is to be used, for use with certain scoping devices the tubular member may have an internal diameter of at least 7 mm, for example at least 8 mm, with the internal diameter typically not exceeding 15 mm, for example not exceeding 14 mm. A cover may have an overall diameter of, for example, 35 to 45 mm, preferably 37 to 43 mm, and may especially have an overall diameter of 39 to 40 mm when at rest and including the projecting elements. The projecting elements may have a length of up to 20 mm, for example from 10 to 18 mm, or 12 to 16 mm. The width of the projecting elements may advantageously be in the region of 1.5 to 3 mm, for example 1.8 to 2.5 mm. The inner longitudinal ridges may be, for example, about 0.1 to 0.3 mm wide. The outer ridges are thicker, for example 0.3 to 0.6 mm in width, and are separated by a web of 0.3 to 0.5 mm in width. The projecting elements may be of any suitable shape, for example, they may be tapered and/or may be of uniform or non-uniform thickness. The cover may if desired comprise projecting elements of differing diameters, lengths, numbers in rings and where present rows of rings may be differentially spaced apart in a non-uniform manner.

The preferred dimensions may vary according to the type of endoscopy for which the cover is to be used. For example, for use in enteroscopy, the dimensions may be essentially the same as those for a sigmoidoscopy cover, although it may be advantageous for the projecting elements to be shorter, for example from 8 to 14 mm or from 8 to 12 mm in length.

The dimensions of the cover can be adapted for other procedures, for example, a larger diameter may be required for a cover for some colonoscopes.

Advantageously, the cover comprises from three to ten projecting elements, each of said projecting elements having a respective detent and being associated with a respective contact region. Advantageously, the cover is monolithic.

The cover may be made by any suitable method for forming of polymer materials, including especially methods suitable for forming of thermoplastic elastomers. Advantageously the cover is formed by injection moulding. In one preferred embodiment, the cover is injection moulded in one piece.

The illustrative covers shown in the drawings and described below are suitable for production using injection moulding in a single shot moulding process, with a line of draw permitting the cover to be formed and removed in a single piece. Whilst manufacture using a single polymer material in a one-shot process offers particular advantages in terms of simplicity and speed of manufacture, other methods are possible. For example, in some embodiments it may be desirable to use a first shot of a first polymer and a second shot of a second polymer, with optional further shots of further polymers, in order to generate desired different characteristics in different regions of the cover. In one illustrative example, a distal part of the cover including the projecting elements may be made of a first polymer, and the proximal part of the cover of a different polymer, for example of a polymer of slightly greater hardness. In yet another example, the configuration of the detent may be such that there is no line of draw and the device may be made using two or more shots of the same polymer.

Whilst certain embodiments of the invention are described below with reference to illustrative examples having one ring of projecting elements, it is also within the scope of the invention for the cover to further include one or more rings of projecting fingers arranged proximally of said projecting elements. Such additional projecting fingers may be, but are not necessarily, of like structure to the projecting elements described herein. Where a plurality of rings is present, it may be desirable for the projecting elements or fingers of one ring to be shorter or longer than those of another said ring of projecting elements or fingers. Some embodiments may have rings or helical patterns of projecting elements or fingers that alternate in length, or having a length that increases with increased distance from the tip.

The cover of the invention may incorporate further functional features. For example, it may include a radio-opaque dye for easier identification. For example, different colour dyes can be used to indicate different sizes of cover.

The cover may in some embodiments comprise at least one structure that enables deformation of the tubular member to take place preferentially at a location remote from the base portions of the projecting elements. That may in particular enable the cover to be usable on scope tips with different diameters. It may be advantageous, for example, to provide two or more circumferentially spaced regions of the tubular member that are more easily deformable than circumferentially adjacent regions. In that manner it may be possible for stretching of the cover, when mounted on a large scope tip, to be concentrated in regions that are circumferentially spaced from those regions at which the projecting elements are mounted. That can reduce the tendency for stretching of the tubular member to affect the freedom of movement of the projecting elements at the mountings.

In an embodiment, at least one of said projecting elements comprises a measurement scale. In a variant of that embodiment two or more projecting elements with measurement scales may be present, or each projecting element may have a measurement scale. In such embodiments the cover of the invention facilitates the assessment of the size of a structure visualised in a body cavity. Structures that may advantageously be measured using the scale include polyps. Because the scale is provided on a movable projecting element it provides a versatile approach to measurement, since the projecting element is readily movable relative to the distal tip of the scoping device. That enables the distal tip and a projecting element carrying a said scale to be manoeuvred into suitable positions relative to one another and to a structure to be assessed to enable a relatively accurate measurement to be made using the measuring scale on the projecting element. Importantly, in addition to their advantageous manoeuvrability to permit visualisation of a said measurement scale, the projecting elements of the device of the invention can serve to open up areas of tissue when the projecting elements become everted during withdrawal of the scope, allowing improved visualisation of structures that may otherwise be hidden within the folds of tissue. Thus, the combination of effective opening up the folds of tissue together with relative movability of the measurement scale and the lens of the distal tip provide a simple approach to polyp assessment that may be used on a standard scoping apparatus, providing versatility in the direction of measurement as well as reliable measurement. Furthermore, there is no need for advancing of an additional part from the scoping device for effecting measurement—the operator only needs to advance a snare or other cutting device from the scoping device if it is concluded that a polyp is to be removed.

Polymer materials suitable for use in the cover of the invention include those which are suitable for use within a cavity of the human or animal body. The polymer or polymers will also in practice be selected having regard to desired characteristics of the cover, for example, flexibility and elastic deformability. Polymer materials with suitable physical characteristics may include elastomeric polymers including elastomeric polyesters, copolyesters, polyamides, polyolefins, silicones, polyetherketones, natural rubbers, synthetic rubbers, and styrene polymers, and further including copolymers or mixtures of any of the aforementioned.

Advantageously the polymer comprises a thermoplastic elastomer which may, for example, be selected from polyamide elastomers, copolyester elastomers, olefinic elastomers, styrenic elastomers, urethane elastomers and copolymers or mixtures of any of the aforementioned. Illustrative suitable polymers include styrene-olefin block copolymers, for example, styrene-ethylene/butylene-styrene block copolymers or styrene isobutylene styrene block copolymers, and silicone rubbers.

Polymers suitable for use in the cover of the invention, or at least in the parts thereof including the projecting elements, preferably have a shore A hardness not exceeding 60. Advantageously, the cover comprises a polymer material of Shore A hardness from 40 to 60, for example 45 to 55, such materials being suitable for providing an appropriate degree of flexibility of the projecting elements and appropriate stretching properties for facilitating mounting of the cover on a scope. Shore A hardness values referred to herein are as determined according to ASTM D2240. Whereas it is often expedient in practice that the cover is formed from a single polymer material, the cover may instead comprise a first polymer material of first Shore A hardness, and a second polymer material of second Shore A hardness, wherein at least the projecting elements are formed of the first polymer material and the first Shore A hardness is lower than the Shore A hardness of the second polymer material.

Covers of the invention may be suitable for use on enteroscopes, colonoscopes, sigmoidoscopes, gastroscopes, and paediatric models of any of the aforementioned. In use, the cover of the invention is applied to a distal tip portion of the scoping device.

Figure 7:
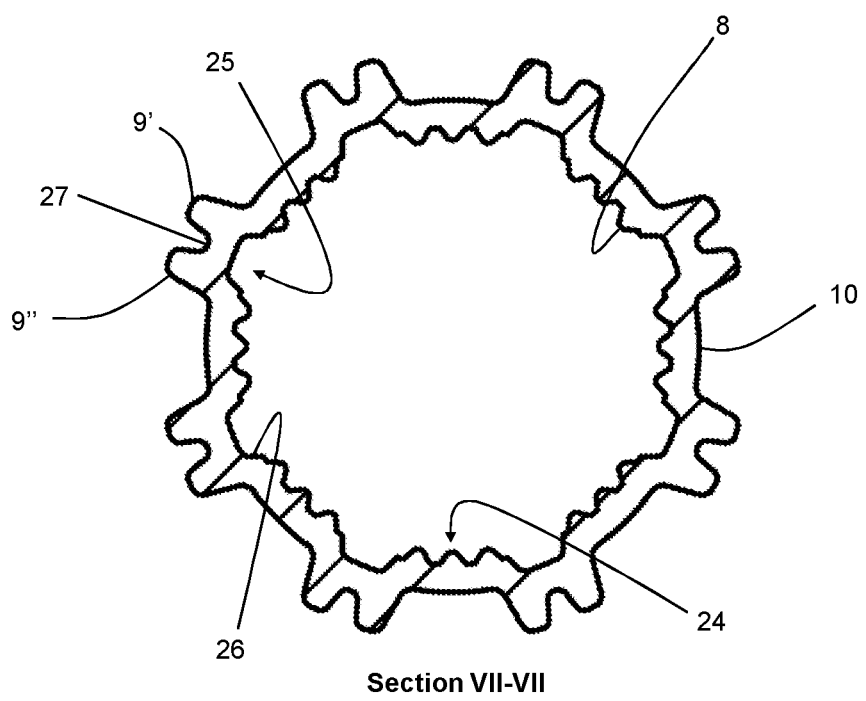
FIG. 7 is a horizontal section along the line VII-VII of FIG. 2.
Figure 8:
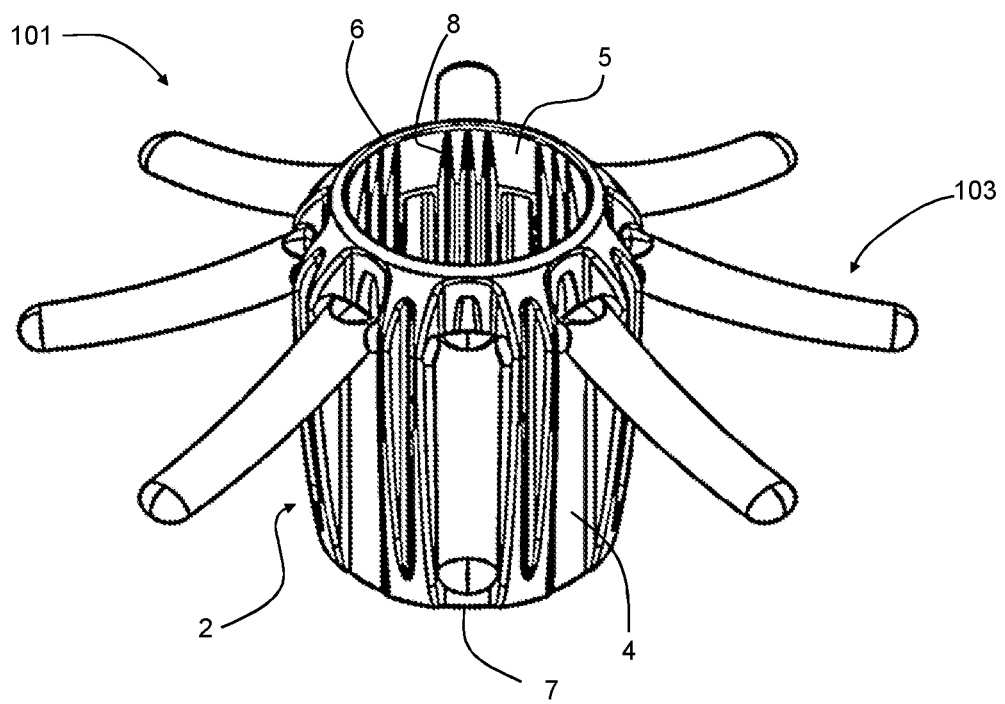
FIG. 8 is a perspective view of cover according to a second embodiment of the invention for use in enteroscopy.
Figure 9:
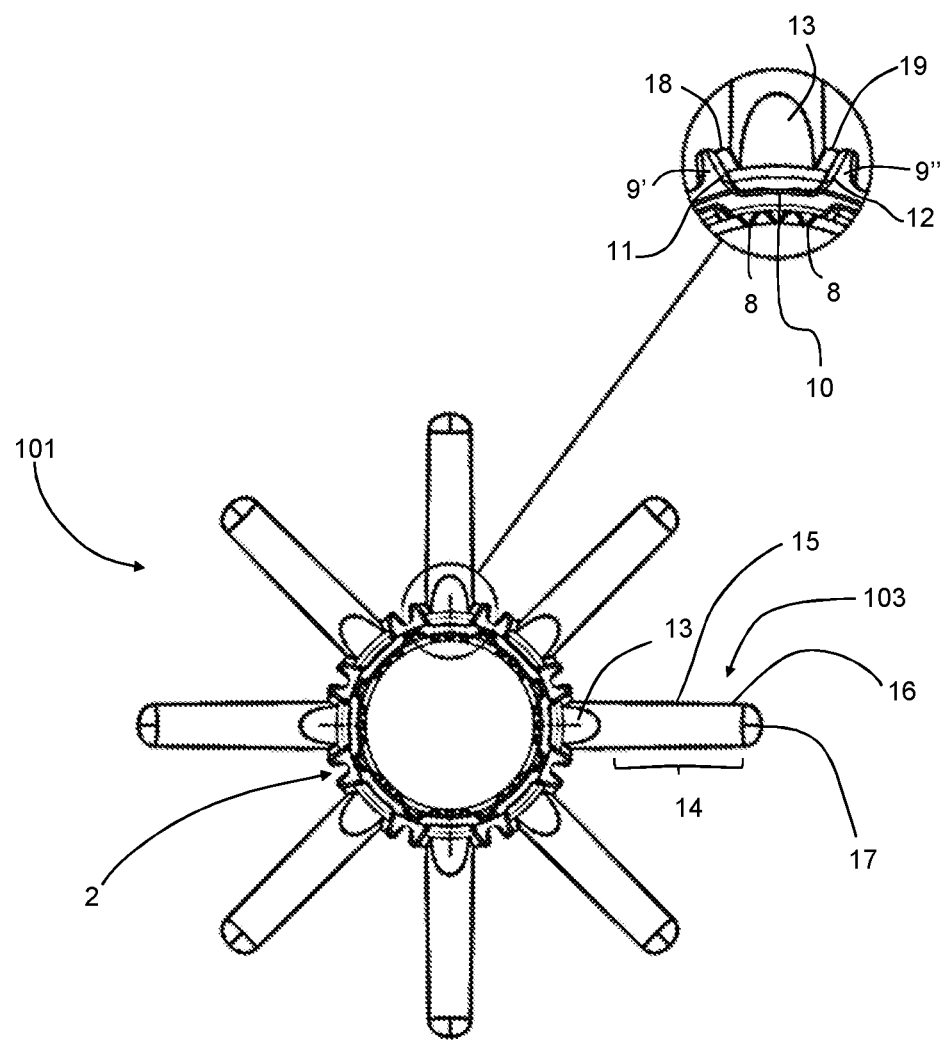
FIG. 9 is a bottom view of the cover of FIG. 8 and includes a detail view showing a portion of the base of a projecting element and the adjacent portion of the tube.
Figure 10:
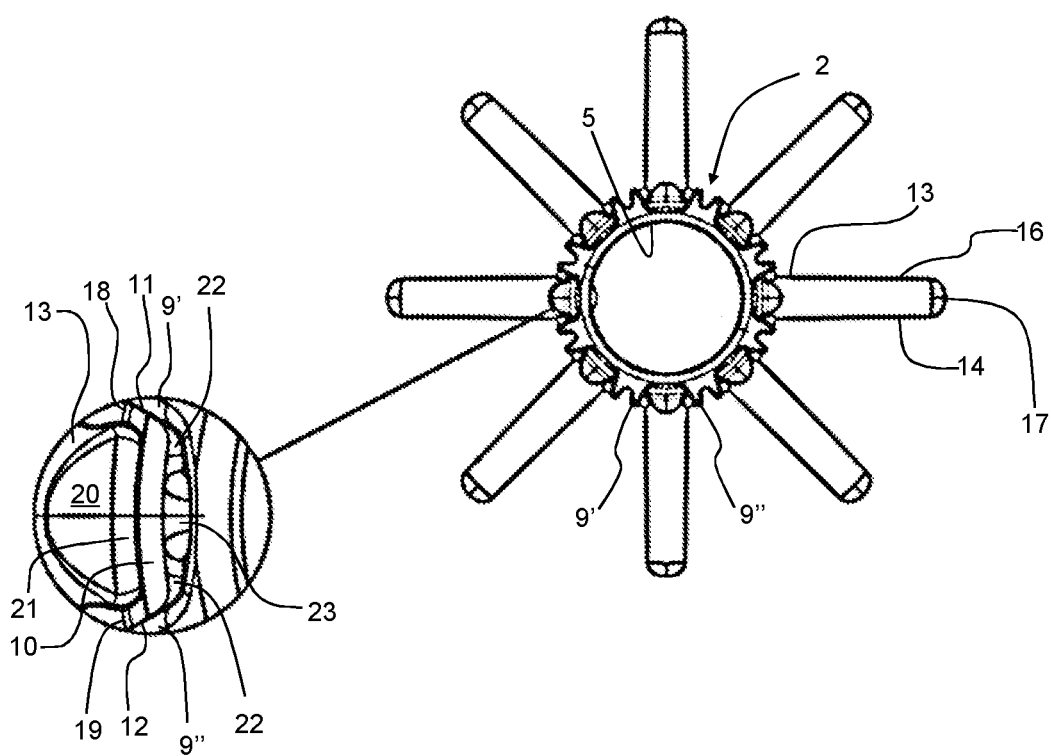
FIG. 10 is a view of the cover of FIG. 1 from above, showing a detail of a portion of the cover at the base portion of a projection element.

The invention is described hereafter with reference to first and second illustrative embodiments of the invention comprising a tip cover device for sigmoidoscopy (FIGS. 1 to 7) and a tip cover device for enteroscopy (FIGS. 8 to 10). The invention may be applied in cover devices suitable for other types of internal examination, for example endoscopy, colonoscopy, and any other technique in which a visualisation device is advanced into a bodily orifice for examination.

FIGS. 1 to 7 show, as a first illustrative embodiment of the invention, a scope cover of dimensions suitable for mounting on the end of a sigmoidoscope. The cover 1 is formed in one piece from a resiliently deformable polymer material. Dimensions referred to herein are, except where otherwise stated, when the cover or parts thereof are in their rest positions, that is, are not subject to any applied deformation.

With reference to FIGS. 1 to 7, the cover 1 has a tubular member 2 generally indicated by reference numeral 2 and eight projecting elements 3. The projecting elements 3 are joined to the tubular member 2 by a mounting structure described further below.

The projecting elements are evenly spaced around the circumference of the tubular member 2 at 45° intervals.

The tubular member 2 comprises a circumferential outer surface 4, a circumferential inner surface 5, a distal edge 6 and a proximal edge 7. The axial length of the tubular member 2 may vary in size relative to the diameter of the tubular member 2.

Irrespective of whether the axial length is longer or shorter than the diameter of the cover, the direction extending parallel to the axis of the tubular member 2 is referred to herein as the longitudinal direction.

The circumferential inner surface 5 has a multiplicity of parallel interior ridges 8 extending longitudinally, which are separated into eight groups of three, which groups are spaced apart about the circumference of the inner surface. The interior ridges serve to improve the grip of the cover when mounted on a scoping device tip, which may especially be useful where the tip is exposed to bodily fluids or other fluids which can have a lubricating effect that has the potential to lead to dislodging of a cover that is not firmly attached.

The circumferential outer surface 4 comprises outer surface ridges 9 extending longitudinally from a location in the vicinity of the distal edge 6 towards the proximal edge 7. The outer surface ridges 9 are arranged in eight pairs, the pairs being spaced apart evenly around the circumference of the tubular member 2. Embraced between each said pair 9', 9" of ridges and the adjacent pairs on each side are channels 10.

Figure 1:
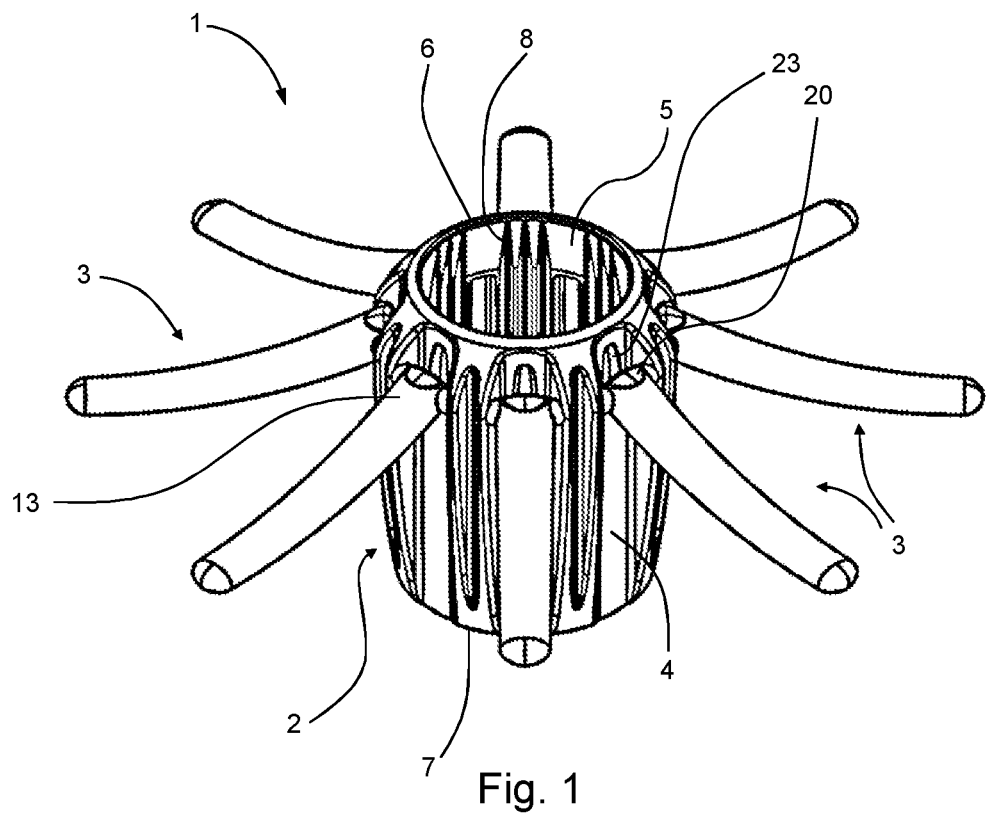
FIG. 1 is a perspective view of cover according to a first embodiment of the invention for use in sigmoidoscopy.
Figure 2:
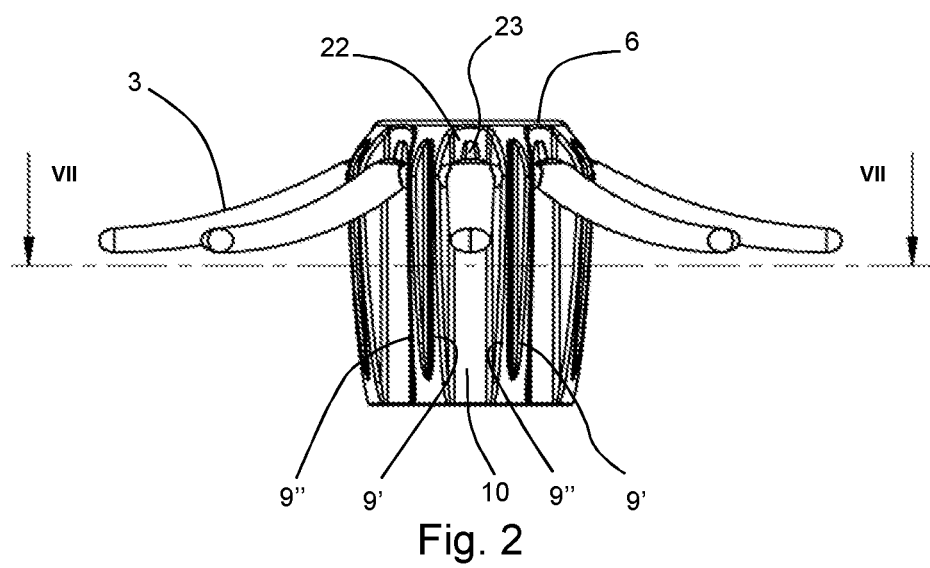
FIG. 2 is a side view of the cover of FIG. 1.
Figure 3:
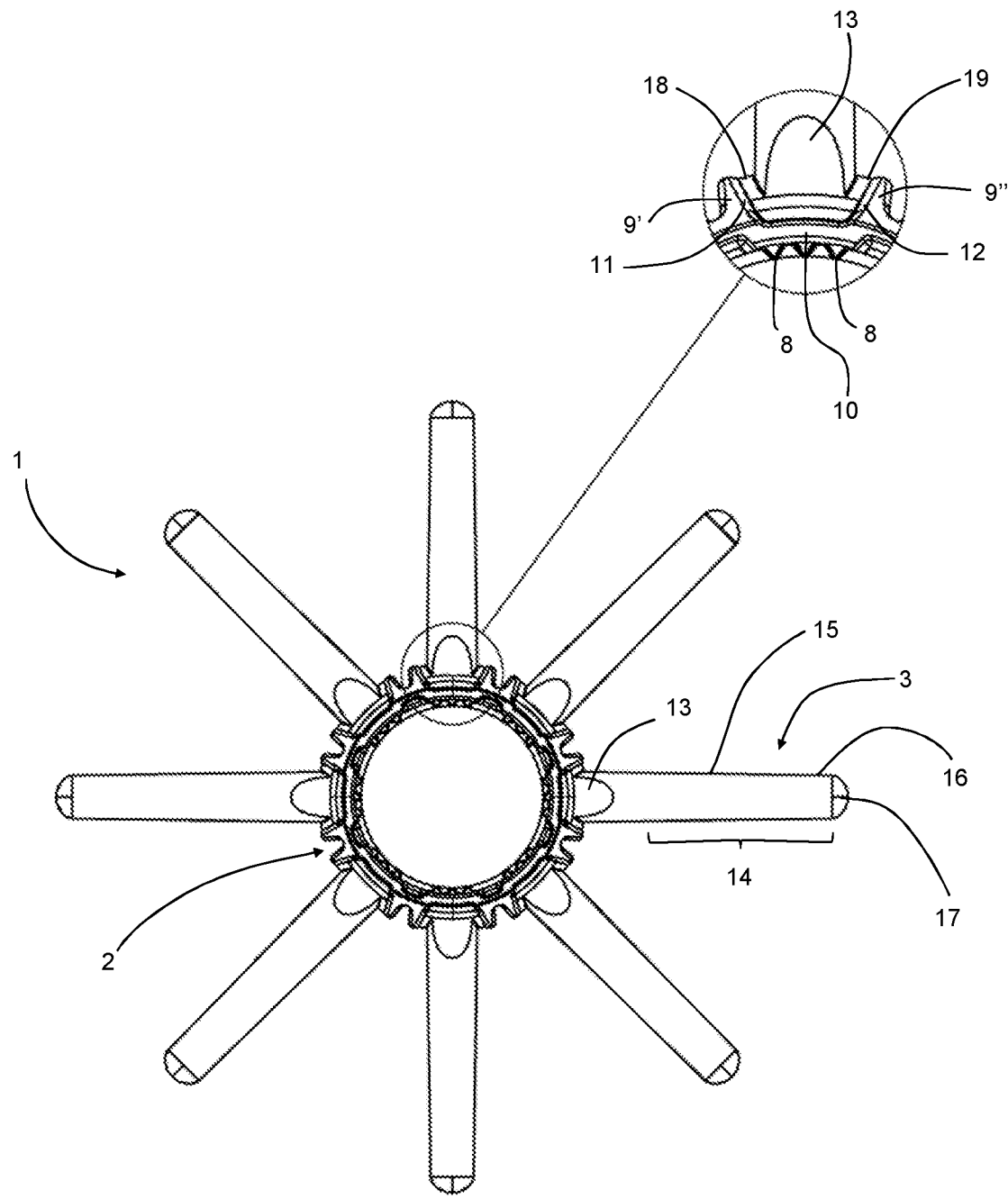
FIG. 3 is a bottom view of the cover of FIG. 1 and includes a detail view showing a portion of the base of a projecting element and the adjacent portion of the tube.
Figure 4:
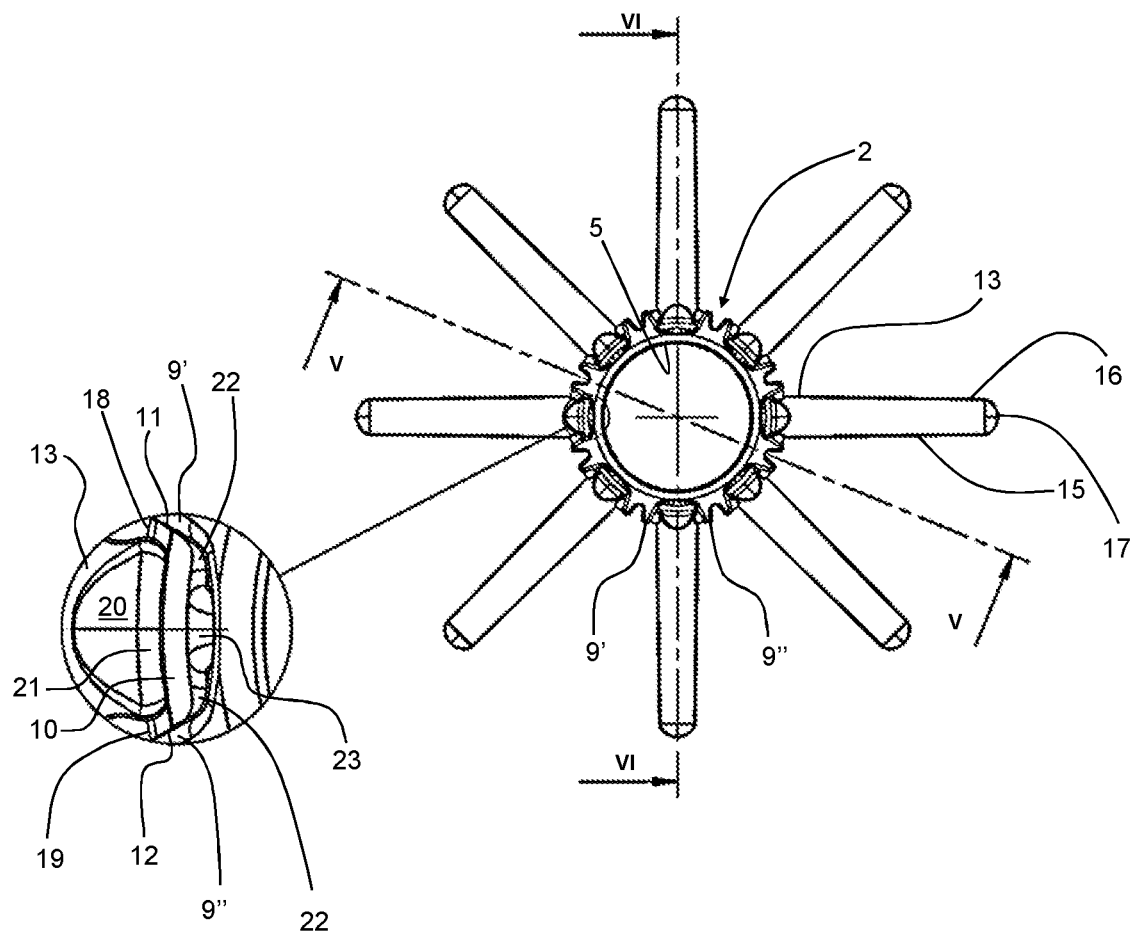
FIG. 4 is a view of the cover of FIG. 1 from above, showing a detail of a portion of the cover at the base portion of a projection element.
Figure 5:
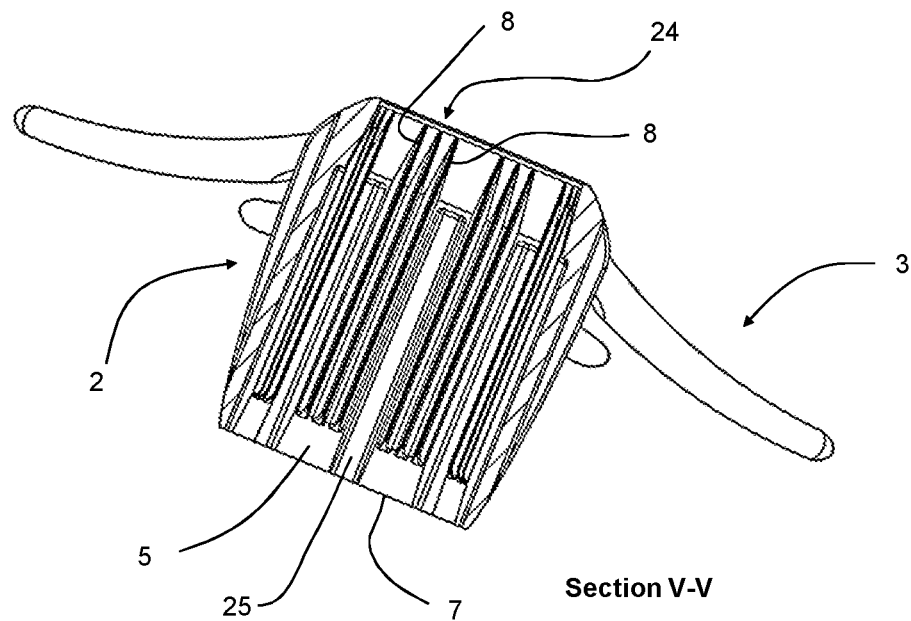
FIG. 5 is a vertical section through the cover of FIGS. 1 to 4 along the line V-V shown in FIG. 4.
Figure 6:
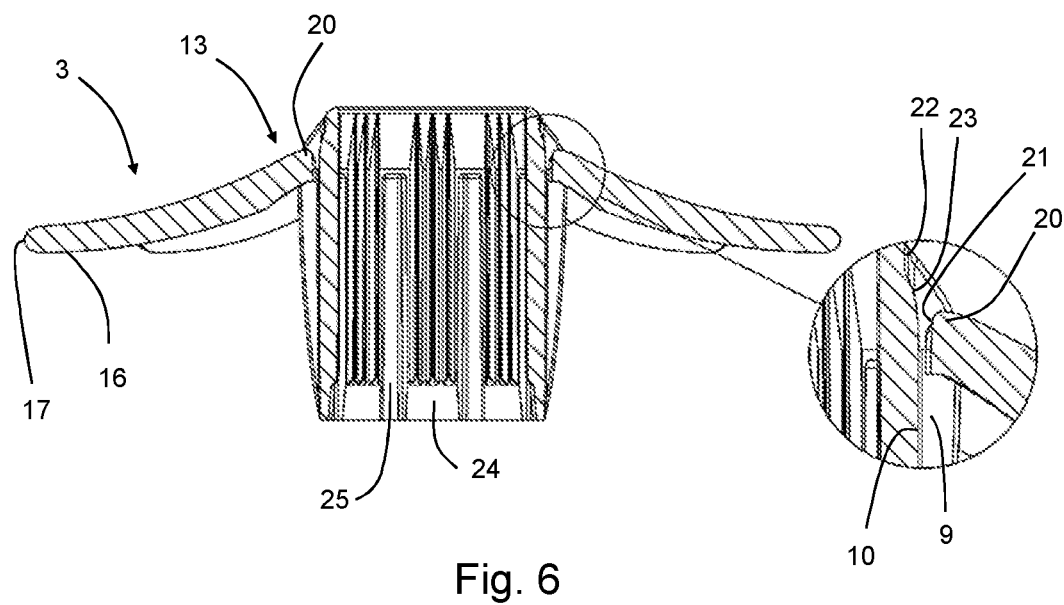
FIG. 6 is a vertical section through the cover of FIGS. 1 to 4 along the line VI-VI shown in FIG. 4, further showing in section a detail of a portion of the cover showing the base portion of the projecting element and the adjacent portion of the tube in section.

With reference to the detail in FIG. 3, each channel 10 is defined by a lateral wall surface 11 of a ridge 9' of one pair, and an opposed lateral wall surface 12 of a ridge 9" of the adjacent pair, the channel 10 having a channel base. The channel serves to receive an associated projecting element in some orientations as hereafter described. The longitudinal outer surface ridges 9 are wider and deeper than the inner surface ridges 8, and in addition to serving to mount the projecting elements 3 the pairs of outer ridges 9 impart additional structural stability with stretching capability of the tube portion in the radial direction as will be described further below, thereby facilitating application to, and removal from, a scoping device.

The structure of one projecting element 3, and associated channel 10 will now be described in more detail. The cover of FIGS. 1 to 7 comprises seven further projecting elements and associated channels which are of like structure and configuration.

The projecting element 3 has a base portion 13 via which the projecting element is mounted on the cover and an arm 14 which extends from the base portion. The arm 14 comprises an intermediate portion 15 and a tip portion 16 terminating in free end 17. The projecting element is of monolithic structure, and the intermediate portion 15 and tip portion 16 are therefore designated for reasons of convenience and do not constitute visibly distinct portions. As previously mentioned, the projecting element 3 is also integrally formed with the rest of the cover in the embodiment described.

The projecting element 3 is connected to the tubular member 2 via a pair of mountings provided on opposite sides of the base portion 13 of the projecting element. A first mounting of said pair comprises a first connector portion 18 extending laterally from a first side of the base portion 13 joining the base portion at one side to the lateral wall surface 11 of ridge 9'. A second mounting of said pair comprises a second connector portion 19 extending laterally from the opposite side of the base portion 13 to the adjacent lateral wall surface 12 of ridge 9". The connector portions 18 and 19 permit pivoting of the projecting element 3 relative to the rest of the cover 1 by means of twisting deformation of the first and second connector portions.

Figure 12:
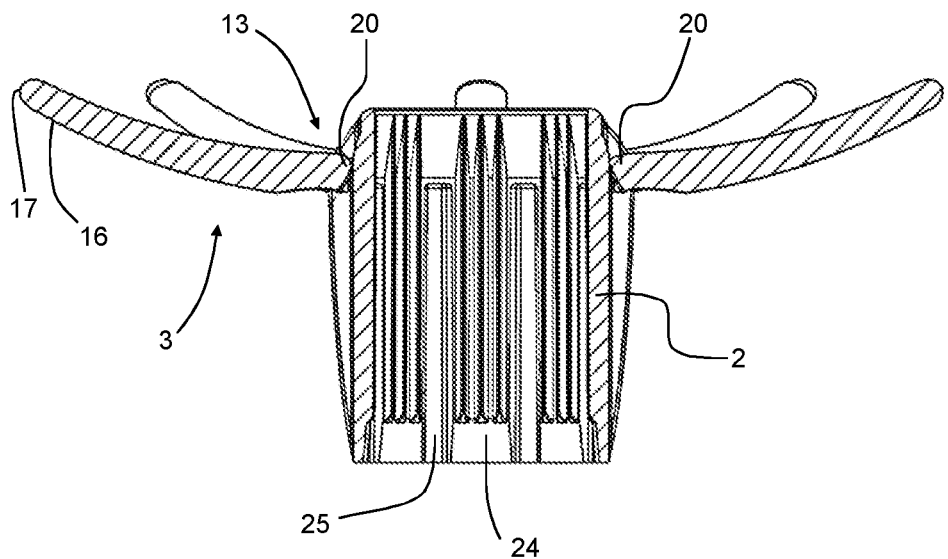
FIG. 12 is a section through the cover of FIG. 11 showing the projecting elements in a forward position.

The connector portions 18, 19 define a pivot axis which extends through the intervening part of the base portion 13 of the projecting element from one connector portion 18 to the other connector portion 19. Pivoting of the projecting element about the pivot axis can occur in two directions. Pivoting movement of the free end 17 towards the proximal direction enables the projecting element to adopt a proximal position in which the projecting element is received at least partly within the channel 10. That position may be adopted on application of force in the proximal direction during insertion of the scope (as shown in FIG. 12) or when folds of the intestinal wall are encountered during advancing of the scope within narrow parts of the body cavity being examined. Pivoting of the free end 17 in the distal direction, as may occur on withdrawal of the scope through the area of the intestine to be visualised, can cause partial eversion of the projecting element from the position shown in FIG. 1 to a forward position in which the free ends of the projecting elements are at an angle of greater than perpendicular relative to the proximal direction. The base portion 13 comprises a detent 20 which is on the opposite side of the pivot axis from the arm 14 of the projecting element. As a result, when the arm 14 comprising the intermediate portion 15 and tip portion 16 is pivoted towards the distal direction, the detent 20 is pivoted downwardly towards the surface of the tubular member 2. The detent 20 includes a contoured contact region 21 which, after a certain degree of pivoting, impacts upon the outer surface of the tubular member 2, within the base of the channel 10. The base of the channel 10 is configured in the embodiment shown to have a contoured region in the vicinity of the base portion 13 of the projecting element 3. The contoured region includes a recessed region 22 and a raised region forming a protuberance 23. The protuberance 23 provides a contact region which obstructs the locus of movement of the detent 20 when the projecting element 3 is pivoted towards the distal direction. In the embodiment shown, the protuberance 23 is essentially level with the part of the floor of the channel 10 that is proximal of the projecting element, and the recessed region 22 around it is recessed relative to the floor of the channel 10. It is also possible, however, for the contact region to be provided on a protuberance 23 at a level that is higher than the proximally located floor of the channel 10. The presence of recessed regions 22 defining between them a protuberance 23, can be advantageous in simplifying mouldability, especially for injection moulding processes where removal from a mould in the line of draw may be facilitated.

In the covers shown in FIGS. 1 to 7 and FIGS. 8 to 10, the rest position of the projecting elements 3 is such that the arm portions are directed slightly proximally, for example at an angle of about 70 to 80° relative to the proximal direction. The detent 20 on the base portion 13 of the projecting element 3, and the protuberance 23 on the tubular member 2 are so arranged relative to one another that contact occurs when the projecting element has been pivoted to be approximately perpendicular or slightly greater than perpendicular relative to the proximal direction. In practice, that may correspond to pivoting the projecting element 3 by about 30° forward from the rest position shown in FIG. 1. Since the cover is of a resiliently deformable material, further advancing of the base portion 13 of the projecting element 3 is permitted by deformation of the detent 20 and/or of the region of contact on protuberance 23. The degree of resistance may increase with the degree of deformation of the contact regions, and further movement may eventually be stopped. In at least some embodiments it is preferred that the advancing of the arm in the distal direction is limited to 120° or less, relative to the proximal direction. For the avoidance of doubt, since the intermediate portion 15 and tip portion 16 of the arm are flexible, bending in the distal direction will be able to occur in those parts, and will occur preferentially in comparison to further bending at the base portion 13 which is subject to the resistance imposed by the contact between the base portion 13 and the cover 2 at protuberance 23. Thus, reference to an angular position relative to the proximal direction is to be taken to refer to the angle of the part of the arm 14 closest to the base portion 13, whilst the remainder of the arm 14 may be subject to additional forward bending.

As shown in FIG. 7, in the rest position the cover comprises longitudinally regions made up of alternating grip regions 24 and expansion regions 25. The grip regions 24 include the inner grip ridges 8 which serve to enhance security of gripping of the cover. Alternating with, and slightly displaced radially outwards relative to, the grip regions 24 are the expansion regions 25 that are located under the pairs of external longitudinal ridges 9. The expansion regions and adjacent grip regions are so joined to one another by inclined web portions 26 that they permit a certain degree of radial expansion of the tubular member 2. Webs 27 of material between each ridge of the outer pairs 9', 9" of ribs also permit a degree of stretching in the distal region of the cover. By comparison, in the channels 10 between adjacent pairs of outer ribs 9, the degree of stretching in the distal region of the cover is limited by the mounting of the projecting elements 3 in the channels between adjacent pairs of outer ribs 9 in that region.

In practice, the cover of FIGS. 1 to 7 for use on a sigmoidoscope may have an internal diameter of from 8 to 10 mm (not including the gripping ridges) when at rest. When mounted on the tip of a scope, the cover will adopt an internal diameter approximating to the external diameter of the scope. The cover may, by way of example, have a total axial length of 15 to 16 mm, an overall diameter of 39 to 40 mm. The projecting elements may have a length of 12 to 16 mm. The width of the projecting elements may advantageously be in the region of 1.5 to 3 mm, for example 1.8 to 2.5 mm. The inner longitudinal ridges may be, for example, about 0.2 mm wide. The outer ridges are thicker, for example about 0.4 mm in width, and are separated by a web of about 0.3 mm in width.

In use, the cover will, when mounted on a scope tip, generally be in a slightly radially expanded configuration, which enhances grip of the cover on the device. In that configuration, the spacing between the base portion 13 and the nearest part of tubular member 2 will be reduced as compared with that shown in the drawings. It may even be possible for the base portion 13 to be in contact with the tubular member 2, provided that the contact does not impede forward pivoting of the projecting element or interaction of the detent 20 with the protuberance 23. The application and removal of the cover 1 to a scoping device is facilitated by stretching of the proximal region of the tubular member 2, where the structure of outer ridges 9, webs 27 and the inclined web portions 26 enhances resilient radial deformation of the tubular member 2. In practice, that is advantageous in that, if the cover is placed on a relatively large-diameter scoping device, the rib pairs 9' 9" are able to pull apart and open up preferentially deforming to maintain the integrity and function of the mountings of the projecting elements and the interaction of the base portion of the projecting elements with the adjacent portions of the tubular member 2. However, the cover is equally usable on a scoping device of relatively small diameter—the rib pairs 9', 9" and intervening web 27 do not need to deform to maintain the integrity and function of the mountings of the projecting elements and the interaction of the base portion of the projecting elements with the adjacent portions of the tubular member 2. Whilst the embodiment described has two parallel ribs 9', 9" defining intervening web 27 it will be appreciated that other structures that focus stretching at regions circumferentially spaced from the mountings of the projecting elements are also possible.

With reference to FIGS. 8 to 10, there is shown an enteroscope cover 101 suitable for mounting over the tip of an enteroscope. The enteroscope cover 101 is of generally similar structure to the sigmoidoscope cover 1. In the cover 101, however, the structure of the projecting elements differs, being somewhat shorter than those of the cover of FIG. 1. Otherwise, the features of the cover 101 are essentially the same as corresponding features of cover 1 as described above and are indicated by the same reference numerals. Although not visible in the drawings, the projecting elements 103 may be slightly wider than those of the cover 1 as well as being slightly shorter. With the exception of the projecting elements, suitable dimensions for the cover 101 may be the same as, or similar to, those for cover 1. The dimensions of the cover can readily be adapted for use with colonoscopes, gastroscopes, and any other type of endosocope.

As previously mentioned, the sigmoidoscope cover of FIGS. 1 to 7 or the enteroscope cover of 8 to 10 is formed of a resiliently deformable material. In the embodiments described in FIGS. 1 to 10, the covers were made of a thermoplastic elastomer, for example Cawiton PR10942E (trade mark), a styrene-ethylene butylene styrene block copolymer of Shore A hardness 46 available from Wittenburg B.V. and suitable for medical use. The covers can be made by any suitable process, with injection moulding being one suitable process for many of the suitable materials. Methods of injection moulding suitable polymers are well-known and widely practised in the art.

Figure 11:
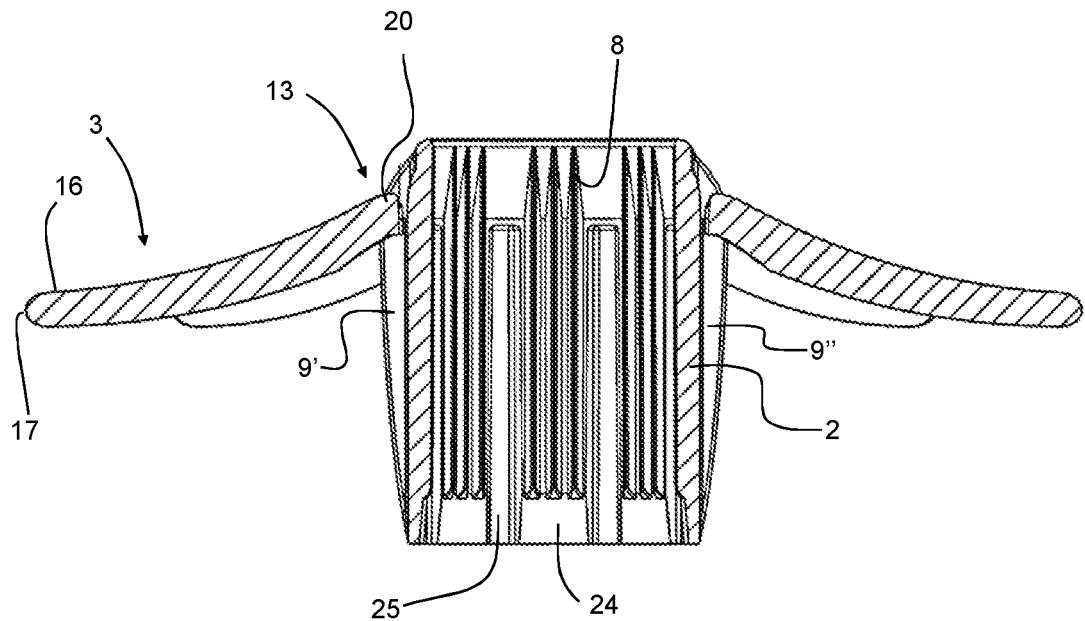
FIG. 11 is a section through a cover according to FIGS. 1 to 7 in the rest position.
Figure 13:
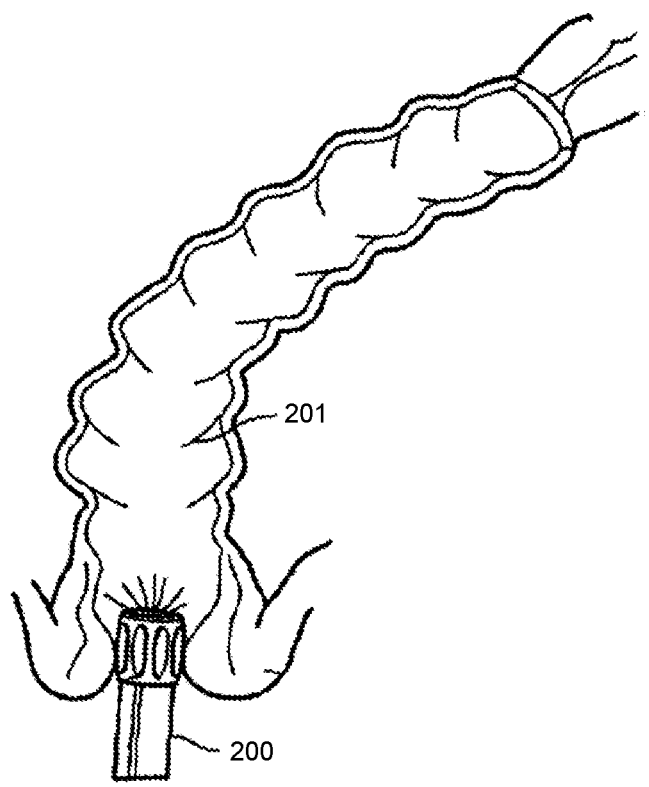
FIG. 13 is a schematic view of a cover according to the invention as used in a first stage of colonoscopic examination.
Figure 14:
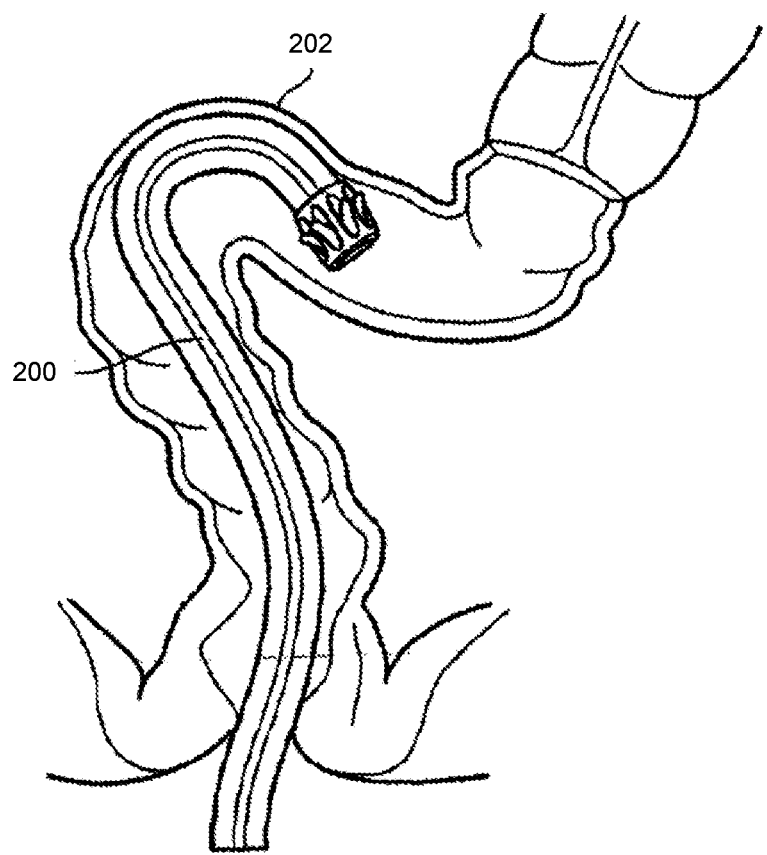
FIG. 14 is a schematic view of the cover of FIG. 13 during a main visualisation stage of a colonoscopic examination.

In use of the cover devices of the invention, advantageous control of the forward movement of the arms is achieved, as illustrated in FIGS. 11 and 12 and with reference to FIGS. 13 and 14. FIG. 11 shows the cover of FIGS. 1 to 7 in the rest position. In practice, it is usual for a scoping device for visualisation of a part of the gastrointestinal system to be advanced relatively quickly through the cavity to be examined until the furthest point requiring examination is reached. The device is then withdrawn more slowly with most of the visual examination being carried out during withdrawal. Since the cover preferably surrounds the tip of the scope very close to the lens system, the clinician's field of view primarily includes the region in front of the distal end 6 of the cover. As the device is withdrawn, the projecting elements encounter structures on the wall of the cavity being examined, such as colonic folds 201 in the case of colonoscopy, and/or encounter bends 202 in the cavity walls (see FIGS. 13 and 14). The relative movement of the scope with reference to those features of the cavity during withdrawal results in the application of a force on the projecting elements tending to push them towards the distal direction with reference to the rest of the cover 1. The projecting elements 3 are able to pivot relatively freely until the contact region 21 of the detent 20 impacts on the tubular member 2 at protuberance 23. As the cover is formed of a resiliently deformable material, the protuberance provides some resistance to further forward movement of the base portion 13 whilst not completely preventing some further forward movement. The movement of the arm 14 is, however, unimpeded, so that further deformation occurs preferentially at intermediate portion 15 and tip portion 16. As a result the projecting elements are able to open up structures for examination whilst minimising any tendency for the free ends 17 to contact the distal edge of the tubular member 2 or to fold over closely against the distal tip of the scope thereby disproportionately and undesirably obstructing the field of view of the scope. The distal edge 6 is bevelled and that further reduces the tendency for undesired contact between the distal edge and the projecting elements.

More specifically, on withdrawal, the projecting elements, acted on by the cavity wall, are urged towards the distal direction. That results initially in relatively free movement towards the distal direction as the base portion is pivoted through a first proximal angular range. However, once the detent 20 reaches a position where it is in contact with the contact region 21 at protuberance 23, the deformation or bending of the intermediate and distal portions of the projecting elements assumes greater importance as further pivoting of the base portion at the mountings is resisted as a result of the contact between the detent 20 and protuberance 23 and relies on deformation or compression of one or both of detent 20 and protuberance 23. However, further distal deflection is still able to occur through bending or deformation of the projecting elements 3 themselves.

Use of a cover of the invention is illustrated with reference to FIGS. 13 and 14 in which colonoscopy is referred to by way of illustration. The distal end tip 200 of the medical scoping device comprises a channel through which a light source, image relaying mean and air suction are supplied. The medical scoping device distal tip 200 with the cover 1 is inserted via the anus into the colon of an individual under investigation. On inserting the medical scoping device with cover into the patient the projecting elements 3 are moved from an at rest position to a second position (referred to herein as a proximal position) where they are flattened towards the medical scoping device shaft. During intubation, the projecting elements 3 are designed to collapse into the channels 10 during insertion through the anus. This exposes a smooth low friction surface of the cover to the mucosa to aid intubation.

The flexible shaft of the medical scoping device 200 is advanced in a distal direction through the colon towards the bend or loop region of the colon (FIG. 14) whilst insufflating the colon immediately forwards of the distal tip of the scoping device 200. The projecting elements once passed the anus revert to their resting first position. As the scope passes further up the colon and encounters the loop region the projecting elements engage with the colon wall in a soft grip (where the projecting elements can fan out and the endoscopist can perform a controlled proximal withdrawal flattening the colonic folds for good visualisation). The projecting elements 3, 103 of the cover of the present invention act to gently open and flatten the colonic folds for inspection during withdrawal.

In that manner, the projecting elements can be used to straighten out loops in the colon for more thorough examination and/or reduce the need for acute tip deflection and/or open out structures such as folds for examination. In accordance with the present invention these objectives are achievable with improved visualisation through reducing encroachment of the projecting elements into the field of vision. Improved visualisation is important for identifying small pre-malignant and malignant lesions that can be hidden or difficult to view when performing conventional endoscopy.

The projecting elements of the cover also serve to gently stabilise the tip of the scoping device within the lumen of the colon or small intestine immediately prior to and during therapeutic procedures. This has the advantage of permitting the endoscopist the reassurance that the tip will remain in position from the stage of visualising a lesion or polyp until completion of the therapeutic procedure.

In use, the projecting elements are designed to pivot forwards so that they become flared outwards on withdrawal. They keep the instrument tip in the central part of the bowel lumen as the instrument moves backwards, gently holding the mucosa to prevent the tip from flipping backwards, they maintain position during therapy and improve all-round visualisation, whilst the possibility of obstruction of the main field of vision in front of the scope tip by one or more projecting elements is reduced.

On withdrawing the scope especially through the anus the projecting elements are able, notwithstanding the limitation on movement of the base portion of the projecting elements, to be moved into a forward position. This is achievable as a result of the flexibility of the arm comprising the intermediate portion 15 and tip portion 16, which permit bending at the intermediate portion and distal portion such that the arm is positioned parallel or nearly parallel to the distal direction. With the arms in that position, the scope can be comfortably withdrawn.

Figure 15:
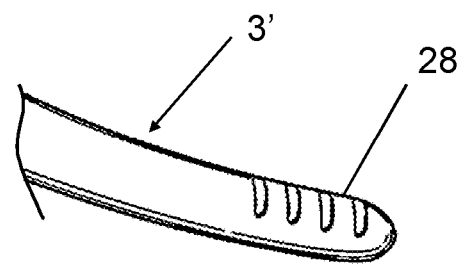
FIG. 15 is a perspective view of a projecting element for use in a cover according to a third embodiment of the invention.
Figure 16:
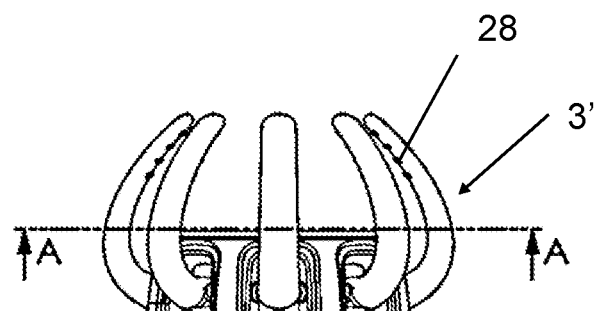
FIG. 16 is a partial side view of the cover of the third embodiment of the invention in which the projecting elements are in an extreme distal position.
Figure 17:
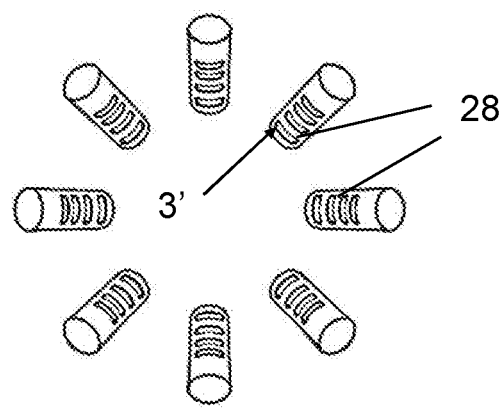
FIG. 17 is a section through the cover shown in FIG. 16 along the line A-A shown in FIG. 16.

FIG. 15 shows a projecting element 3' that may be used in a further embodiment of the cover of the invention. Projecting element 3' is essentially the same as the projecting element 3 as described with reference to FIGS. 1 to 12 above. However, the upper distal surface is provided with a measurement scale 28 comprising four spaced elongate ridges. The measurement scale as shown extends along at least a part of said projecting element in a direction from the base portion towards the distal tip portion of the projecting element. Whilst the measurement scale 28 is shown in FIG. 15 as comprising four spaced elongate ridges it will be appreciated that the measurement scale may be of any suitable form (for example printed) and may extend in a different direction. FIG. 16 shows a distal portion of the cover when in use. The projecting elements 3' are in a measuring, position, in which the free ends are deflected into the field of view. Since the distal pivoting of the base portion of the projecting elements is limited to, for example about 140° relative to the proximal direction, the deflection of the projecting elements into the field of view is achieve at least in part through bending of the intermediate and distal portions of the projecting element. The projecting elements 3' are shown schematically in FIGS. 16 and 17 as being deflected distally with their tips including measurement scales 28 deflected radially inwardly beyond the distal edge of the tubular member. With reference to FIG. 17, which is a section along line A-A in FIG. 16, when the projecting elements are in that position, the measurement scales 28 are comfortably within the field of vision of a scoping device visualisation system in which visualisation takes place from the distal end of the scoping tip portion positioned in the axial channel 18. However, any tendency of the tips of the projecting elements 3' with measurement scales 28 to collapse towards the distal tip surface of the scope is reduced as a result of the limitation on distal pivoting provided by the interaction of the detent 20 and contact region 21 (not visible in FIG. 16). Whilst the measurement scale can be visualised when the projecting elements 3' are inclined at no more than 180°, for example no more than 160° or 140° relative to the proximal direction, visualisation and accuracy of measurement may be further enhanced when the projecting element is deflected further, as shown in FIGS. 16 and 17.

In FIGS. 16 and 17 and also in each of FIGS. 11 and 12 respectively, for ease of illustration, the cover device is shown with all projecting elements deflected distally to the same extent. In practice, it is possible for the degree of distal deflection to be different in different projecting elements 3, 3', for example according to the proximity to, and local configuration of, the cavity wall. If desired, the distal tip carrying the cover may be so manoeuvred relative to the colon wall such that one or more of the projecting elements 3, 3' is intentionally caused to be deflected by a greater amount than other projecting elements 3, 3'.

Distal deflection of the projecting elements 3, 3' is a consequence of interaction between the free ends and the surrounding wall regions of the cavity being examined during the withdrawal of the distal tip of the scope through the body cavity. Radial inward deflection may be induced for one or more of the projecting elements 3, 3' by means of manoeuvring the endoscope relative to adjacent structures within the cavity being examined, for example, by controlling the position and motion of the distal tip portion 200 remotely such that one or more said projecting elements contacts a wall region of the cavity, the relative movement of the distal tip of the scope 200 and the cavity wall serving to deflect the projecting element(s) 3, 3'. In the embodiment of FIGS. 16 and 17, each of the projecting elements 3' is provided with its own measuring scale 28. Whilst in principle the invention includes devices in which a single measuring scale is provided on one of a plurality of projecting elements, providing measuring scales on all projecting elements enables measurement to be carried out with any projecting element 3' so that the device can readily be used to measure a polyp at any angular location of the inner wall of the body cavity without the need for significant pivoting of the endoscope tip to bring a single measurement scale into a suitable angular location. Embodiments having a measurement scale advantageously enable assessment of the size of an anatomical abnormality in an elongate body cavity, which abnormality may at least in part be visually obscured by a movable obstruction. In practice this may be achieved by advancing towards said abnormality a scoping device 200 having a distal tip portion comprising the cover, if necessary manoeuvring the distal tip portion such that one or more of the projecting elements 3' contacts said movable obstruction so as to move said obstruction relative to said abnormality to be assessed; further manoeuvring said distal tip portion such that a said projecting element is positioned adjacent to said abnormality; assessing a dimension of said abnormality by comparison of said object with a said measurement scale 28 on the adjacent projecting element; and optionally surgically removing said abnormality.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A cover for a shaft of a medical scoping device, the cover comprising a tubular member arranged for application over a distal end of the medical scoping device shaft with the tubular member, in use, extending along a portion of the length of the distal end of the shaft, the tubular member comprising a proximal circumferential edge, a distal circumferential edge, an inner surface at least a part of which grips the shaft, and an outer surface, the cover comprising a plurality of projecting elements spaced apart circumferentially around the tubular member, each projecting element having a base portion and an arm portion, the base portion comprising first and second mountings by which the projecting element is pivotably mounted on the tubular member about a pivot axis, wherein the base portion comprises a detent, and wherein the tubular member comprises a contact region, said contact region comprising a protuberance and being so located that pivoting movement of the projecting element for moving the arm portion in a distal direction can effect impacting of said detent on said protuberance, and the detent is located on an opposite side of the pivot axis from said arm portion.

2. The cover according to claim 1, wherein at least one of said detent and said contact region is resiliently deformable.

3. The cover according to claim 1, wherein said protuberance comprises a portion that extends distally beyond the base portion of the projecting element.

4. The cover according to claim 1, wherein the contact region is integrally formed with the tubular member, or wherein the contact region and the projecting elements are integrally formed with the tubular member.

5. The cover according to claim 1, wherein the respective contact region is so located relative to the respective projecting element that it delimits the locus of movement of at least the base portion of the said projecting element.

6. The cover according to claim 1, wherein the cover comprises from three to ten projecting elements, each of said projecting elements having a respective detent and being associated with a respective contact region.

7. The cover according to claim 1, wherein the projecting elements are spaced apart in a ring around the tubular member, and optionally, wherein the ring is spaced from the distal edge of the tubular member by a distance that is less than the length of the projecting elements, or wherein the ring is located no more than 10 mm from the distal edge of the tubular member.

8. The cover according to claim 1, wherein the cover comprises on its outer surface a multiplicity of channels extending axially relative to the tubular member, each channel being defined between a pair of axially extending channel walls, and each projecting element being mounted in one of said channels, or wherein each projecting element is mounted between a said pair of channel walls by means of first and second mounting members attached to opposed sides of the base portion of the projecting element and each connecting said base portion to a respective one of said pair of channel walls, and optionally wherein each contact region is provided in a respective channel.

9. The cover according to claim 8, further comprising a multiplicity of spaced longitudinally extending ridges the said channel walls being formed by lateral surfaces of a respective said longitudinally extending ridge.

10. The cover according to claim 1, wherein the or each projecting element comprises a distal tip portion and an intermediate portion between said base portion and said distal tip portion, the base portion, intermediate portion and distal tip portion being resiliently deformable.

11. The cover according to claim 1, wherein each projecting element is movable from a resting position to a proximal position in which its distal tip portion is directed in a proximal direction towards a proximal end of the scoping device shaft and is movable in a distal direction to a forward position in which the detent of the base portion of the respective projecting element abuts the corresponding contact region.

12. The cover according to claim 11, wherein, on movement of the projecting element to said forward position, the detent impacts on the corresponding contact region when the projecting element is at an angle of from 80° to 140° relative to the proximal direction, whereby the contact region impedes further forward movement of the base portion beyond said angle.

13. The cover according to claim 11 wherein the detent is so arranged and so movable relative to the contact region that on moving towards the forward position the detent first impacts on the contact region when the base portion of the projecting element is at an angle of from 90° to 160° relative to the proximal direction and the detent and/or contact region are resiliently deformable to permit further forward movement of said base portion through an angle of at least 10°, and optionally, the detent of the projecting element first impacts on the corresponding detent when the projecting element is at an angle of from 90° to 120° relative to the proximal direction, and/or the detent and contact region are so arranged that distal movement of said base portion beyond 160° is prevented.

14. The cover according to claim 1, wherein the cover is of one or more resiliently deformable polymer materials, or wherein the cover is of an elastomeric polymer selected from elastomeric polyesters, copolyesters, polyamides, polyolefins, silicones, polyetherketones, natural rubbers, synthetic rubbers, and styrene polymers, and copolymers or mixtures of any of the aforementioned, and optionally, wherein the elastomeric polymer is selected from styrene-olefin block copolymers and silicone rubbers.

15. The cover according to claim 1, wherein the cover comprises a polymer material of Shore A hardness from 40 to 60.

16. The cover according to claim 1, wherein the cover comprises a first polymer material of first Shore A hardness, and a second polymer material of second Shore A hardness, wherein at least the projecting elements are formed of the first polymer material and the first Shore A hardness is lower than the Shore A hardness of the second polymer material.

17. The cover according to claim 1, wherein the cover is monolithic.

18. The cover according to claim 1, wherein the cover is injection moulded in one piece.

19. The cover according to claim 1, further comprising one or more rings of projecting fingers arranged proximally of said projecting elements.

20. The cover according to claim 1, further comprising a radio-opaque dye.

21. The cover according to claim 1, wherein the projecting elements have a length of from 10 to 20 mm.

22. The cover according to claim 1, comprising at least one structure that enables deformation of the tubular member to take place preferentially at a location remote from the base portions of the projecting elements.

23. The cover according to claim 1, wherein the cover is suitable for mounting on a distal tip of a scoping device selected from enteroscopes, colonoscopes, sigmoidoscopes, gastroscopes, paediatric enteroscopes, paediatric colonoscopes, paediatric sigmoidoscopes, and paediatric gastroscopes.

24. The scoping device comprising a cover according to claim 1.

25. A cover for a shaft of a medical scoping device, the cover comprising a tubular member arranged for application over a distal end of the medical scoping device shaft with the tubular member, in use, extending along a portion of the length of the distal end of the shaft, the tubular member comprising a proximal circumferential edge, a distal circumferential edge, an inner surface at least a part of which grips the shaft, and an outer surface, the cover comprising a plurality of projecting elements spaced apart in a circumferentially extending ring around the tubular member, each projecting element having a base portion and being pivotably mounted on the tubular member via said base portion, and the cover comprising a protuberance provided on the tubular member of the projecting element, the protuberance being so located on the outer surface of the tubular member that it is impacted upon by said base portion on pivoting of the projecting element towards a distal direction, wherein the cover comprises on the outer surface a multiplicity of channels extending axially relative to the tubular member, each of the multiplicity of channels being defined between a pair of axially extending channel walls, the base of each of the multiplicity of channels comprising a contoured region including a recessed region and a raised region forming the protuberance.

26. A method of examining a cavity of a human or animal body, comprising insertion of an endoscopy device comprising the cover according to claim 1, and causing everting of the projecting elements of said cover, wherein the angle of inclination of the projecting elements when everted is limited to not more than 140°.

* * * * *